United States Patent
Barhak

(10) Patent No.: US 10,923,234 B2
(45) Date of Patent: Feb. 16, 2021

(54) ANALYSIS AND VERIFICATION OF MODELS DERIVED FROM CLINICAL TRIALS DATA EXTRACTED FROM A DATABASE

(71) Applicant: Jacob Barhak, Austin, TX (US)

(72) Inventor: Jacob Barhak, Austin, TX (US)

(*) Notice: Subject to any disclaimer, the term of this patent is extended or adjusted under 35 U.S.C. 154(b) by 1002 days.

(21) Appl. No.: 15/466,535

(22) Filed: Mar. 22, 2017

(65) Prior Publication Data

US 2017/0286627 A1    Oct. 5, 2017

Related U.S. Application Data

(60) Provisional application No. 62/315,578, filed on Mar. 30, 2016, provisional application No. 62/326,052, filed on Apr. 22, 2016.

(51) Int. Cl.
| | |
|---|---|
| *G16H 50/50* | (2018.01) |
| *G06N 3/06* | (2006.01) |
| *G06N 3/00* | (2006.01) |
| *G06N 5/00* | (2006.01) |

(52) U.S. Cl.
CPC ............ *G16H 50/50* (2018.01); *G06N 3/006* (2013.01); *G06N 5/003* (2013.01)

(58) Field of Classification Search
CPC ........ G16H 50/50; G16H 50/20; G16H 40/63; G16H 50/30; G16H 20/17; G16H 20/40; G16H 30/20; G16H 10/40; G16H 10/60; G16H 15/00; G16H 30/40; G06Q 30/0601; G06Q 30/02; G06Q 10/04; G06Q 30/0202; G06Q 30/0241; G06Q 30/0254; G06Q 30/0269

USPC ............................................................. 705/2
See application file for complete search history.

(56) References Cited

U.S. PATENT DOCUMENTS

| | | | | |
|---|---|---|---|---|
| 9,858,390 | B2* | 1/2018 | Barhak | G16H 50/50 |
| 2005/0004789 | A1* | 1/2005 | Summers | G06Q 30/02 |
| | | | | 703/22 |
| 2005/0102044 | A1* | 5/2005 | Kohn | G05B 13/024 |
| | | | | 700/28 |
| 2007/0294110 | A1* | 12/2007 | Settimi | G16H 10/60 |
| | | | | 705/3 |
| 2009/0150134 | A1* | 6/2009 | De Leon | G16H 40/20 |
| | | | | 703/11 |
| 2012/0271612 | A1* | 10/2012 | Barsoum | G16H 50/50 |
| | | | | 703/11 |
| 2017/0132357 | A1* | 5/2017 | Brewerton | G16H 50/50 |

* cited by examiner

*Primary Examiner* — Trang T Nguyen
(74) *Attorney, Agent, or Firm* — Schwegman Lundberg & Woessner, P.A.

(57) ABSTRACT

This disclosure describes frameworks and techniques directed to the analysis and verification of models extracted from a database. In some cases, the database can include an online database, such as clinicaltrials.gov administered by the United States National Institutes of Health. In particular, this disclosure describes implementations that utilize models derived from clinical trial data extracted from a database and analyzes the models. The analysis of the models can be used to verify the results of the clinical trials from which the models were derived. Additionally, the analysis of the models can identify a combination of models that can be used to predict health outcomes of one or more biological conditions for one or more populations.

20 Claims, 7 Drawing Sheets

ANALYSIS AND VERIFICATION OF MODELS DERIVED FROM CLINICAL TRIALS DATA EXTRACTED FROM A DATABASE

CROSS-REFERENCE TO RELATED APPLICATIONS

This application claims priority to U.S. Provisional Patent Application No. 62/315,578 entitled "The Reference Model for Disease Progression Using Object Oriented Population Generation" filed on Mar. 30, 2016, and to U.S. Provisional Patent Application No. 62/326,052 entitled "The Reference Model for Disease Progression Using Model Combination" filed on Apr. 22, 2016, both of which are incorporated by reference herein in their entirety.

BACKGROUND

Databases can store data related to various types of information. In some cases, a database administrator can provide an interface by which users can access the data stored in a database and can provide the data in a format that makes the data easy to manipulate and store outside of the data base. In other cases, the extraction and utilization of data obtained from a database can be a resource intensive procedure.

In some particular situations, data related to clinical trials can be stored in a database. Clinical trials are performed by scientists on a population of subjects often to study an aspect of health. In various situations, a clinical trial can examine how behaviors, diet, medications, and the like can influence an aspect of human health. The clinical trials document characteristics of the population participating in the clinical trials. The clinical trials can also indicate the effect that particular behaviors, diet, and/or medications have on the populations that are the subjects of the clinical trials. Additionally, the clinical trials can provide models based on the data obtained from the clinical trials. where the models can indicate the amount of influence that a particular variable has on one or more aspects of the health of individuals. The models can also indicate the progression of a disease in individuals and provide information about the transitions between one state of a disease to another. The models derived from clinical trials often indicate assumptions made by the scientists conducting the research about the progression of a disease.

Clinical trials can provide useful information to the public about behaviors, diet, and/or medications that can influence the health of individuals. In addition, access to clinical trial data can be used to test the efficacy of the models derived from the clinical trial data. The amount of clinical trial data available to the public has been on the increase. In a particular example, the website clinicaltrials.gov provided by the United States National Institutes of Health provides a repository for storing clinical trials data that is accessible to the public. However, the extraction and manipulation of data from databases storing clinical trial data can present challenges.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

FIG. 5A and FIG. 5B show examples of using gradient descent techniques to determine a minimum for an aggregate fitness function that identifies the contributions of each individual model to the aggregate fitness function.

DETAILED DESCRIPTION

Figure 1:
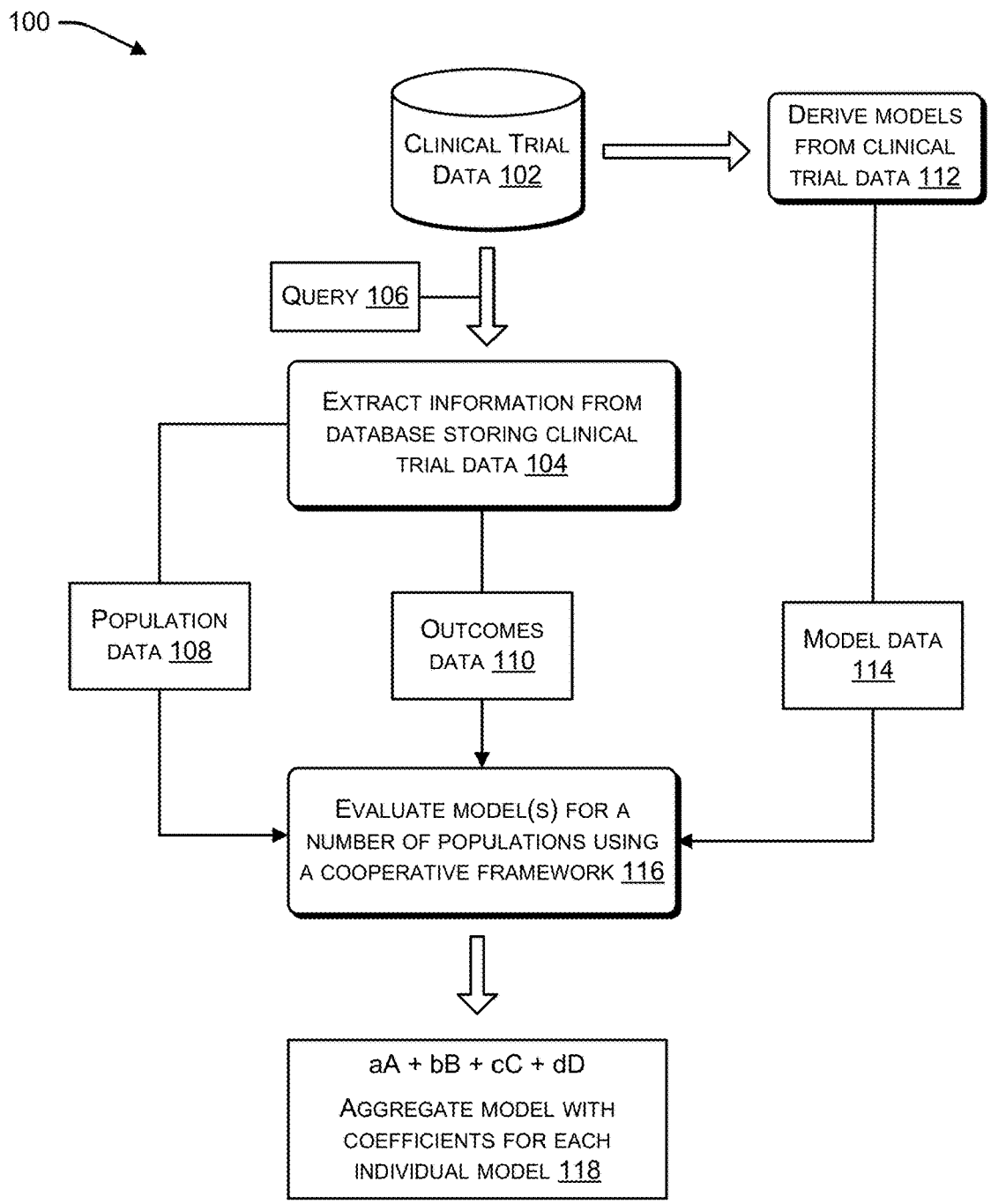
FIG. 1 shows a schematic diagram of an example framework to determine the fitness of clinical trial models to predict the progression of a biological condition.

This disclosure is directed to the analysis and verification of models derived from data extracted from a database. In particular, this disclosure describes implementations that extract clinical trial data from a database and analyze models derived from clinical trials data. The analysis of the models can be used to verify the results of the clinical trials from which the models were derived. Additionally, the analysis of the models can identify a combination of models that can be used to predict health outcomes of one or more biological conditions for one or more populations.

In particular, the implementations described herein include extracting data related to clinical trials from a database storing clinical trial data. In some cases, the data extracted from the database can correspond to clinical trials that were conducted with respect to one or more biological conditions. Additionally, the data extracted from the database can correspond to one or more populations. Clinical trial data can be extracted from a database based on a query. In some cases, the query can include a text query that includes keywords that are used to identify clinical trials corresponding to the keywords. In particular implementations, specific instructions can be accessed during the extraction of information from a clinical trials database to extract particular information from the clinical trials database. For example, instructions can be accessed during the extraction of clinical trials data to specifically obtain population data from clinical trials that correspond with a query. To illustrate, a query can be provided that is related to obtaining data from clinical trials where diabetes was studied and instructions can be utilized to extract characteristics of the populations of those clinical trials, such as age, weight, biological indicators (e.g., cholesterol levels, high density lipoprotein (HDL) levels, etc.). The use of particular sets of instructions to extract data from a clinical trials database can reduce the computing resources used to obtain specific information from the clinical trials database. In some implementations, the extraction of clinical trial data from one or more databases can take place in multiple phases. In particular implementations, a first phase can include extracting information related to a number of clinical trials from a database, while a second phase can include filtering the extracted information based on a particular filtering criteria.

Observed data obtained from clinical trials, can be used to evaluate the various models derived from multiple other datasets. A model can be evaluated using a number of populations that can have at least some characteristics that are different from the population that participated in the clinical study that was used to derive the model. The results from the evaluation can be compared against observed outcomes from the same clinical trial or from different clinical trials to determine a fitness of the model for predicting outcomes for a biological condition associated with the model. In previous situations, a competitive framework was utilized to compare the fitness of different models based on evaluating the models with a set of populations. However, the competitive framework utilized large numbers of memory and processing resources that continued to increase as the number of models being evaluated increased. In particular, the amount of computing resources and memory resources utilized to evaluate models derived from clinical trial data increases close to exponentially as the number of models being evaluated increases.

In contrast to previous scenarios, the implementations described herein utilize a cooperative framework in conjunction with some competitive elements in the evaluation of models described from clinical trial data. In particular, a linear combination of models can be evaluated with the contribution of each of the models being indicated by a coefficient associated with the model. The minimum for the linear combination of models can be determined in order to evaluate the coefficients for each model that provide the best fitness for predicting the progression of a biological condition. The coefficients that have the greatest contribution to the linear combination can be identified as the models that have the best fitness for predicting the progression of a biological condition. In some particular implementations, gradient descent techniques can be utilized to evaluate the linear combination of models. By utilizing a cooperative framework with some competitive elements to evaluate the fitness of models derived from clinical trials data rather than a competitive framework, the number of processing and memory resources increases at merely a linear rate per iteration when the number of models being evaluated increases as opposed to an almost exponential rate. Additionally, a cooperative framework with some competitive elements can identify information about models derived from clinical data that a competitive framework is unable to identify. For example, a cooperative framework with some competitive elements can determine a combination of models that can effectively predict the progression of a biological condition and the contributions of each model to the combination. Conversely, a framework that is simply competitive can merely be used to identify the performance of a single model with respect to other individual models, but does not provide any indication as to how the models that predict the same phenomenon can be combined to provide a composite model to predict the progression of a biological condition nor can the competitive model that is discrete by choice of model be as accurate as a cooperative model that merges models continuously.

The evaluation of models derived from clinical trial data for the purposes of predicting disease progression can be performed by generating a number of populations from the clinical trial data and evaluating various models in light of characteristics of the different populations. In some cases, certain models may have a higher fitness than other models with respect to different populations. To generate the populations used to evaluate models derived from clinical trial summary data, characteristics of various populations can be analyzed and virtual populations can be generated from the actual populations that participated in the clinical trials. Access to personalized clinical trial data is restricted, yet summary data is available publicly and unrestricted. Therefore, generating a synthetic population increases the amount of information available to model. In this way, the aggregate population from a number of different clinical trials can be utilized to determine a number of virtual populations that can be used to evaluate models that predict the progression of a biological condition, where the virtual populations can have different characteristics from the clinical trial populations. For example, a virtual population used to evaluate models predicting the progression of diabetes can have blood pressure, age, triglyceride, HDL, and low density lipoprotein (LDL) distributions that are derived from a number of clinical trial populations, but do not actually match the populations that participated in the clinical trials, although describing similar statistics.

In generating the virtual populations used to evaluate models that predict the progression of a biological condition, object oriented techniques can be implemented. For example, objects can be created that include characteristics of one or more populations that participated in one or more clinical trials. To illustrate, an object can be created that includes rules that generate distributions for age, gender, height, and weight for a population that participated in a clinical trial that is considered a default for a population. In another example, an object can be created for another population that indicates an objective from the clinical data associated with the population. In this way, a virtual population can be generated using the characteristics of one clinical trial population and an objective of another clinical trial population by creating an object for the virtual population that inherits the population characteristic generating rules from the first population that is considered as representing the default population structure and the objective from the second population representing specific summary statistics found in a certain trial. By allowing populations to be generated using object oriented techniques, the implementations described herein enable flexibility in the characteristic generating rules and objectives utilized to generate virtual populations and also result in reducing the amount of computing resources utilized to generate a population. In particular, rather than recreating the characteristics and/or objectives of each clinical trial population utilized to generate a new, virtual population, the objects associated with the clinical trial populations can simply be inherited by the object of the new, virtual population. Furthermore, characteristics that may be missing from a particular population can be filled in by inheriting the missing characteristics from another population. This adds to the flexibility of the implementations described herein with respect to conventional techniques that are limited in the way that population characteristics can be combined to generate a virtual population used to evaluate the fitness of models that predict the progression of biological conditions.

Furthermore, the simulations that are performed with respect to the evaluations of the aggregate models can be performed concurrently and using parallel computing techniques. The concurrent processing of simulation and the using multiple processors in parallel reduces the amount of time needed to evaluate the aggregate models.

FIG. 1 is a schematic diagram of an example framework 100 to determine the fitness of clinical trial models to predict the progression of a biological condition. The framework 100 includes clinical trial data 102. The clinical trial data 102 can be stored in one or more databases. The clinical trial data 102 can be accessible by computing devices via an interface. In some cases, the interface can include a webpage that enables access to the clinical trial data 102 being stored by the one or more databases. In other implementations, the clinical trial data 102 can be accessed via a computing device application. In particular, the clinical trial data 102 can be accessed using an app executing on a mobile computing device, such as a tablet computing device or a smartphone.

The clinical trial data 102 can include information related to clinical trials that have been conducted by scientists and/or scientific organizations. The clinical trials can be related to various biological conditions. In some scenarios, the biological conditions can include diseases. In particular implementations, the biological conditions can be related to a level of an analyte present in subjects of the clinical trials. In some situations, the clinical trials can examine the effects of one or more factors on a biological condition. The factors can include characteristics of subjects participating in the clinical trials, such as age, weight, gender. The factors that can affect a biological condition can also include levels of analytes measured in subjects. For example, factors that can affect a biological condition can include cholesterol levels, triglyceride levels, HDL levels, LDL levels, and the like. Additionally, the factors that can affect a biological condition can include behaviors of subjects participating in clinical trials. To illustrate, the factors can include information related to diet (e.g., servings of fruits and/or vegetables per day), exercise, sleep, and so forth.

The framework 100 includes, at 104, extracting information from a database storing the clinical trial data 102. The information can be obtained through a query 106. The query 106 can include one or more keywords that can form the basis of a search of the clinical trial data 102. In some cases, the query 106 can include keywords directed to a particular biological condition. In additional situations, the query 106 can include keywords related to characteristics of populations participating in clinical trials. The query 106 can also include keywords corresponding to factors that can affect the progression of a biological condition. In an illustrative example, the query 106 can include keywords corresponding to diabetes, heart attack, and/or stroke. In this situation, clinical trials that include the keywords diabetes, heart attack, and/or stroke will be identified in the clinical trial data 102.

The extraction of information from the clinical trial data 102, at 104, can include parsing one or more databases that store the clinical trial data 102 for clinical trials that include one or more keywords of the query 106. Additionally, after identifying clinical trials that correspond to the query 106, particular information can be extracted from the clinical trial data 102. For example, instructions can be involved in the extraction of information from the clinical trials data 102 that cause certain portions of information included in individual clinical trials to be extracted, while leaving behind other portions of information included in the individual clinical trials.

In the illustrative example of FIG. 1, the information extracted from the clinical trials data 102 can include population data 108 and outcomes data 110. The population data 108 can include information related to the populations that participated in the individual clinical trials that provided the clinical trial data 102 including baseline population distributions. The outcomes data 110 includes results from the clinical trials. In some examples, the outcomes data 110 can include information indicating a progression of a biological condition for one or more populations that participated in clinical trials. To illustrate, the outcomes data 110 can indicate mortality of individuals that participated in clinical trials. In other illustrative examples, the outcomes data 110 can indicate occurrences of biological conditions, such as stroke or myocardial infarction.

At 112, the framework 100 can include deriving models from the clinical trial data 102. The models can be included in model data 114 that can be evaluated according to implementations described herein. In various implementations, the models can be stored in one or more databases. The models can be accessed online and retrieved manually, in some cases, or via an automated process in other situations. The model data 114 can include information directed to the models derived from the results of the individual clinical trials. The models can represent a series of assumptions about the progression of a biological condition being studied in a clinical trial for the population that participated in the clinical trial. In some cases, the model data 114 can indicate a probability of a transition between states of a disease. In a particular example, the model data 114 can indicate a probability of an individual included in a certain population moving from a state of no stroke to a state of stroke or a probability of an individual included in a certain population moving from no heart disease to myocardial infarction. In particular implementations, the model data 114 can include one or more equations that can be used to predict the progression of a biological condition.

At 116, the framework 100 can include evaluating models for a number of populations using a cooperative framework with some competitive elements. The models being evaluated can be obtained from the model data 114. In addition, the populations utilized to evaluate the models can be generated from the population data 108. In some cases, aggregated information obtained from each of the populations included in the population data 108 can be used to generate virtual populations that are used to evaluate the models. The evaluation of the models can include generating a number of virtual populations and running simulations based on the models and the virtual populations. The simulations can produce predictions of the progression of a biological condition with respect to each of the individuals included in the virtual populations. The progression of the biological condition for each individual included in the virtual populations can be determined by running the simulations over a number of years and determining the probability that the individual will progress to various states of the disease as the age of the individual increases.

In various implementations, the models can be evaluated according to a cooperative framework. The cooperative framework can include determining how the different models can work together and evaluating the fitness of the individual models based on the contributions of the individual models to the overall prediction of the progression of a biological condition. In some cases, the cooperative framework can include evaluating a linear equation that includes variables that represent each model being evaluated and a coefficient for each model that indicates the contribution of the corresponding model in predicting the progression of the biological condition. The linear equation can be optimized to determine the coefficients for the models. In particular implementations, gradient descent techniques can be utilized to determine the local minimum of the linear equation.

In the illustrative example of FIG. 1, the evaluation of the models using a cooperative framework can produce an aggregate model 118 with coefficients indicating the contribution of each individual model. The aggregate model 118 is represented as $aA+bB+cC+dD$, where A, B, C, D are functions that represent the individual models and a, b, c, d are the coefficients indicating the influence of the individual models A, B, C, and D on the prediction of the progression of a biological condition. In an illustrative implementation, models, A, B, C, and D can predict the progression of diabetes and the aggregate equation $aA+bB+cC+dD$ can also be used to predict the progression of diabetes. Additionally, the coefficients a, b, c, d can sum to 1 and the individual coefficients can have values ranging from 0 to 1. The coefficients with values closer to 1 have more influence over the prediction of progression of a biological condition than coefficients with values closer to 0.

Observed outcomes from actual clinical trials that are included in the clinical trial data 102 can be used to determine the coefficients for each model. That is, by comparing the predictions of the progression of a biological condition generated by the models being evaluated with actual observed outcomes, a fitness of each model for predicting the progression of the disease can be determined. The closer that the predictions of a model are to the observed outcomes, the greater the contribution of the individual model in the aggregate model.

In some instances, competitive aspects can also be incorporated into the framework 100. For example, certain initial conditions can be provided that are used in a first iteration of the aggregate equation 118 before the optimization of the aggregate equation 118. For example, the initial conditions can indicate values for individual coefficients of the aggregate equation 118. In particular implementations, different initial conditions for the evaluation of the aggregate equation 118 can produce different values for the coefficients of the aggregate equation 118 after the optimization process. To illustrate, a first coefficient can have a first value (e.g., 0.2) for a first set of initial conditions and the first coefficient can have a second value (e.g., 0.3) for a second set of initial conditions. The results of the optimization of the respective sets of initial conditions can be evaluated with respect to the outcomes 110 and then compared to one another. In this way, the fitness of the aggregate model 118 with regard to different sets of initial conditions can be evaluated with respect to one another and a set of values for the individual coefficients of the aggregate equation 118 having a best fitness can be determined.

Figure 2:
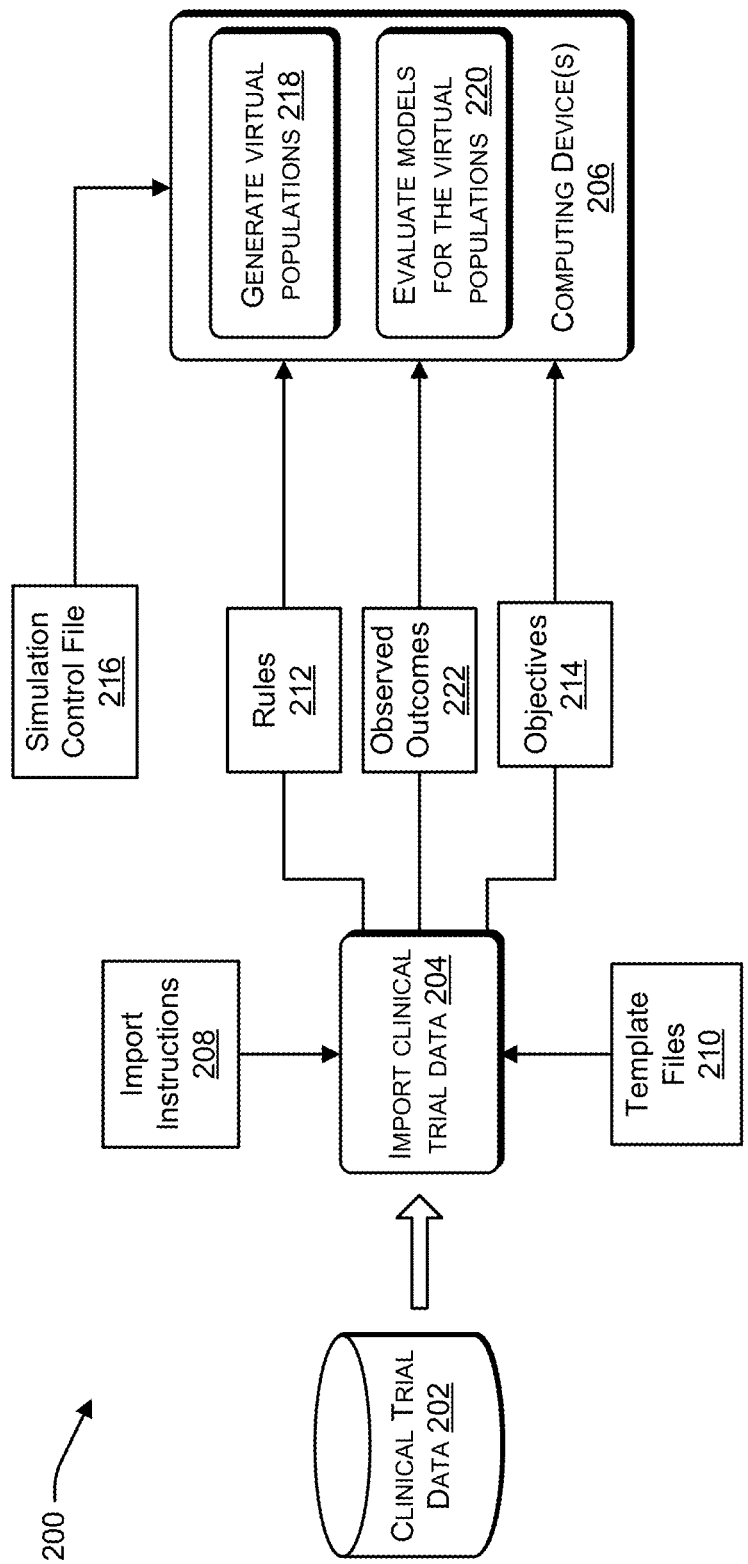
FIG. 2 shows a schematic diagram of a framework for extracting information from clinical trials data to generate populations used to evaluate models that predict the progression of a biological condition.

FIG. 2 includes a schematic diagram of a framework 200 for extracting information from clinical trials data to generate populations used to evaluate models that predict the progression of a biological condition. The framework 200 includes clinical trial data 202 that is stored in one or more databases. In some cases, the clinical trial data 202 can be similar to or the same as the clinical trial data 102 of FIG. 1. In various implementations, the clinical trial data 202 can be stored as extensible Markup Language (XML) data that can be parsed and extracted for use by various computing devices.

At 204, the framework 200 includes importing the clinical trial data 202. In particular implementations, the clinical trial data 202 can be imported to one or more computing devices 206. The one or more computing devices 206 can include software and/or one or more applications that can process the clinical trial data 202 that has been imported. The clinical trial data 202 can be imported utilizing import instructions 208 and/or template files 210. The import instructions 208 can include information used to obtain particular information from the clinical trial data 202 such as population data, duration of clinical trials, inclusion/exclusion criteria, and data indicating the outcomes of the clinical trials. Other information can be extracted, as well, from the clinical trial data 202 according to the import instructions 208, such as clerical information related to the clinical trials (e.g., description of the clinical trial).

In some implementations, the import instructions 208 can be related to different phases of the process to import portions of the clinical trial data 202. For example, in a first phase of data extraction, the import instructions 208 can filter the clinical trials obtained from the clinical trials data 202 in response to a query to obtain particular clinical trials data 202. In particular, the import instructions can extract titles of clinical trials, a description of the clinical trials, a duration of the clinical trials, and so forth, and provide this information to one or more template files 210. The template files 210 can store information obtained from the clinical trials data 202 in a particular format. In various situations, the template files 210 that include information obtained from the clinical trials data 202 in the first phase of data extraction can be analyzed to narrow the clinical trials from which to obtain data in subsequent phases of data extraction. To illustrate, a computing device or a computing device user can review a list of clinical trials produced during the first phase of data extraction to identify clinical trials to target in subsequent phases of data extraction based on a set of criteria.

In a second phase of importing clinical trials data 202, information from the subset of clinical trials identified in the first phase of information extraction is obtained. In the second phase of importing clinical trials data 202, the import instructions 208 are directed to extracting population information from the identified subset of clinical trials. The population information extracted from the clinical trials data 202 can include information that can be used to generate virtual populations that are used to evaluate the effectiveness of models associated with the clinical trials data 202. In some examples, the population information can include age, gender, physical characteristics (e.g., height, weight), dietary information, behavioral information (e.g., smoker/non-smoker, exercise habits), analyte levels (e.g., cholesterol level, HDL level, LDL level, triglycerides), other physical data (e.g., blood pressure, pulse rate), and so forth. The portions of the clinical trial data 202 imported in the second phase of information importation can be stored in additional template files 210 that are designed to hold the population data. Additionally, code can be generated for the population data extracted from the clinical trials data 202 indicated inheritance characteristics of population data. That is, inheritance code can indicate whether or not the information obtained with respect to a particular population can be used in conjunction with information obtained with respect to another population to generate a virtual population that can be used to evaluate models obtained from the clinical trial data 202. For example, inheritance code generated in conjunction with the extraction of information from the clinical trials data 202 can indicate that weight and height information from one clinical trial can be utilized in conjunction with age and triglyceride levels from another population to produce an aggregate virtual population.

Additional import instructions 208 can be utilized in a third phase of data importation to extract outcome data from the subset of clinical trials identified in the first phase of importing clinical trials data 202. In particular implementations, the import instructions 208 of the third phase of importing clinical trials data 202 are directed to extracting information from the clinical trials data 202 that indicates the states and/or characteristics of individuals that participated in the clinical trials. For example, the outcomes data for clinical trials related to heart disease may indicate the number of participants that suffered a heart attack in the duration of the clinical trial and/or the number of participants that suffered a stroke during the clinical trial. Previously observed outcomes extracted from the clinical trials data can be stored in particular template files 210 to be merged with newly extracted observed outcomes data 222 and used to validate the outcomes produced by models that are being evaluated.

In each phase of data extraction from the clinical trials data, the import instructions 208 and the template files 210 can differ. The template files 210 provide the extracted information in specific forms that are easily accessible and manipulatable by software executing on the computing devices 206 that is used to evaluate the models included in the clinical trials data 202.

In some implementations, the import instructions 208 can also include manipulation commands that process the extracted portions of the clinical trials data 202. The manipulation commands can include text processing commands. In particular implementations, the text processing commands can be related to handling Unicode and joining, replacing, and filtering text extracted from the clinical trials data 202. The import instructions 208 can also include conversion code that caused data extracted from the clinical trials data 202 to be converted into a standardized form. For example, the units for reporting levels of analytes in subjects can be different from clinical trial to clinical trial. In an illustrative example, the import instructions 208 can include code for converting mg/dL to mmol/L for HDL and triglycerides because the coefficients for this conversion can differ for HDL measurements and triglycerides measurements. In this way, the conversion of units can be flexible and context-aware. That is, based on the context of the values provided, certain conversion factors can be selected to produce the appropriate final values after the conversion takes place. The import instructions 208 can be used to modify, if necessary, information extracted from the clinical trials data 202 to match the standardized units of the import instructions 208 otherwise conversion will match the units in the template file 210. In another example, the import instructions 208 can include code for converting race and/or ethnicity information into a standardized format due to the variety of formats that clinical trials can report this type of information.

The import instructions 208 can also be utilized to generate code that can be utilized to generate individuals included in virtual populations that are used to evaluate models for predicting the progression of a biological condition. In some implementations, rules 212 and objectives 214 can be generated based on information obtained from the clinical trials data 202. The rules 212 and the objectives 214 can be used during the generation of virtual populations that can be utilized to evaluate models derived from the clinical trial data 202. In some cases, the rules 212 can include parameters that can be utilized in generating virtual populations for models related to a particular biological condition. For example, the rules 212 can indicate that a virtual population is to include individuals within a certain age range and exclude individuals outside of that age range. In a particular illustrative example, the rules 212 can indicate that individuals under the age of 18 and over the age of 65 are not to be included in a virtual population. Additionally, the objectives 214 can indicate statistical distributions for a virtual population. To illustrate, the objectives 214 can indicate that a particular percentage of a virtual population is to have a level of an analyte within a specified range. In an illustrative situation, the objectives 214 can indicate that 50% of a virtual population is to have a blood pressure from 140 mmHg to 180 mmHg.

In some cases, the rules 212 and objectives 214 can be updated as new clinical trials are added to the clinical trial data 202. In particular, as new clinical trials that satisfy the conditions of a query are added to the clinical trials data 202, the import instructions 208 can be implemented to import portions of the new clinical trials and store the newly imported information into the template files 210. The newly imported information can be stored in the template files 210 in conjunction with the information originally stored in the template files 210. In particular implementations, the rules 212 and the objectives 214 can also be modified to correspond with the changes to the clinical trial data 202 brought about by the new information added to the clinical trials data 202.

A simulation control file 216 can also include information used to generate virtual populations and evaluate models indicating the progression of biological conditions. The simulation control file 216 can include information including the models to be evaluated, populations for the models to be evaluated against, and how to evaluate fitness of the models. The simulation control file 216 can also include inclusion/exclusion criteria for the model and population combinations to be simulated. Further, the simulation control file 216 includes instructions for coefficient optimization, such as stopping criteria (e.g., when to stop the optimization process), coefficient change methods and parameters between optimization iterations, and one or more initial conditions for optimization. The simulation control file 216 can also indicate that some coefficients can be static during the optimization process.

After obtaining the rules 212 and the objectives 214, the computing device(s) 206 can, at 218, generate one or more virtual populations. The virtual populations can include individuals that satisfy the rules 212 and the objectives 214. In particular implementations, the virtual populations generated by the computing device(s) 206 can have characteristics that correspond with the aggregate characteristics of actual populations studied in the clinical trials included in the clinical trials data 202.

At 220, the computing device(s) evaluate the models obtained from the clinical trials data 202 in light of the virtual populations generated at 218. That is, individual models obtained from the clinical trials data 202 are used to predict the progression of a biological condition for each individual included in the virtual populations. In particular implementations, simulations using the individual models are performed for the virtual populations to determine the outcomes for each individual with respect to the progression of a biological condition. The results of the simulations can be compared to the observed outcomes 222 that are obtained from the clinical trials data 202 to determine a fitness of a particular model to predict the progression of the biological condition.

In various implementations, each model is evaluated in light of multiple virtual populations. Additionally, multiple simulations can be run for each virtual population with respect to the individual models. In some cases, the fitness of a model to predict the progression of a biological condition can be determined using a cooperative framework where a number of models are evaluated together. The models can be evaluated by producing an aggregate model comprised of the individual models and determining the relative contributions of each individual model to the aggregate model.

Figure 3:
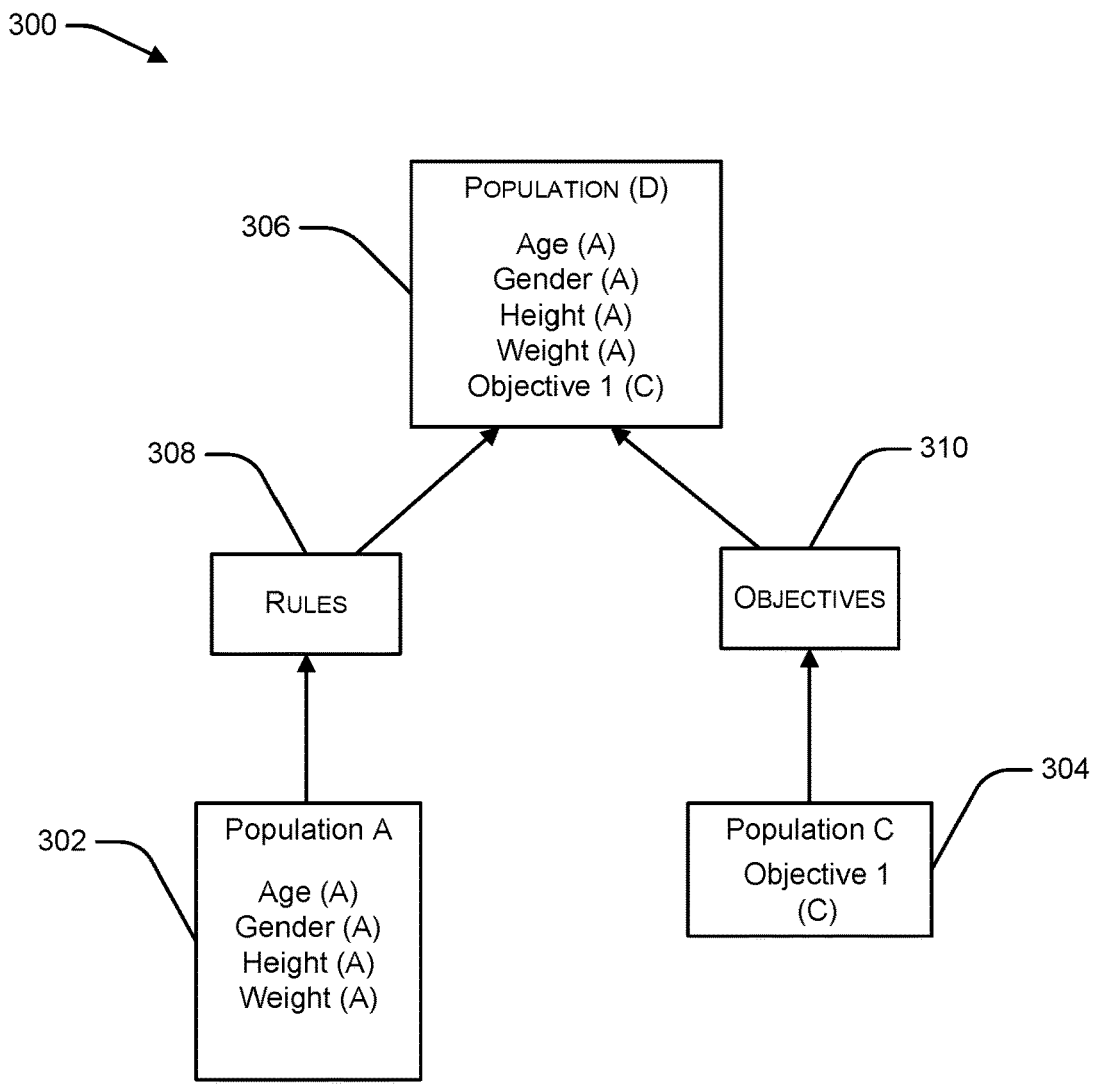
FIG. 3 shows a schematic diagram of a framework showing the use of object oriented techniques to generate virtual populations used to verify models derived from clinical data.

FIG. 3 includes a schematic diagram of a framework 300 showing the use of object oriented techniques to generate virtual populations used to verify models derived from clinical data. In particular, the framework 300 includes a first population object 302 corresponding to a first population and a second population object 304 corresponding to a second population. The first population and the second population can each relate to a group of individuals that participated in a clinical trial. The population objects 302, 304 can include characteristics of the individuals included in the respective populations associated with the objects 302, 304. The characteristics can be represented by ranges, averages and standard deviations, distributions, combinations thereof, and the like. For example, the characteristics can be related to one another by arithmetic operations and other functions, such as one or more characteristics depending on gender or blood pressure. In the illustrative example of FIG. 3, the first population object 302 corresponds to the first population having characteristics corresponding to age, gender, height, and weight. Additionally, the second population object 304 corresponds to an objective of the second population. The objective relates to target values for a characteristic of a virtual population. To illustrate, an objective can indicate a mean and standard deviation for a characteristic, such as age, blood pressure, height, weight, etc. for a given virtual population.

The framework 300 also includes a third population object 306 that inherits rules 308 from the first population object 302 and objectives 310 from the second population object 304. The third population object 306 includes age characteristics, gender characteristics, height characteristics, and weight characteristic generated from the rules 308 associated with the first population object 302 and objective 1 inherited from the objectives 310 associated with the second population object 304.

In additional implementations, a population can inherit data from one or more additional populations. The data can include characteristics of individuals included in the one or more additional populations and can be extracted after generation of a population defined by rules and objectives. In some cases, the one or more additional populations can include individuals from at least one virtual population. In other situations, the one or more additional populations can include individuals from at least one actual population that participated in a clinical trial. In various implementations, characteristics of an additional population can override one or more characteristics of another population, such as one or more characteristics of population A or population D. In these scenarios, the values of the characteristics (e.g., age, weight, height, etc.) of the additional population can replace the values of the characteristics of the original population. In particular implementations, characteristics of an additional population can fill in missing values of characteristics of a population. For example, population D does not include blood pressure information. In this situation, an additional population that includes blood pressure information can provide this information that is inherited by population D.

The ability for populations to inherit values of characteristics, objectives, or both from other populations provides flexibility in the generation of new populations that is not found in conventional population generation techniques. Further, the ability for populations to inherit values of characteristics, objectives, or both from other populations can lead to generating more complete populations by filling in missing data for some populations. In this way, populations can be generated that include characteristics that more closely correspond with the populations used to generate certain models. For example, if a model was generated from a population that measured HDL levels, but a population being used to evaluate the model does not include individuals with HDL data, the HDL levels of individuals from an additional population that includes values for HDL levels can be used to fill in the missing data. In this way, the framework of using object-oriented techniques to provide data to populations is different from conventional techniques that do not provide methods to fill in and substitute values for characteristics of populations.

Figure 4:
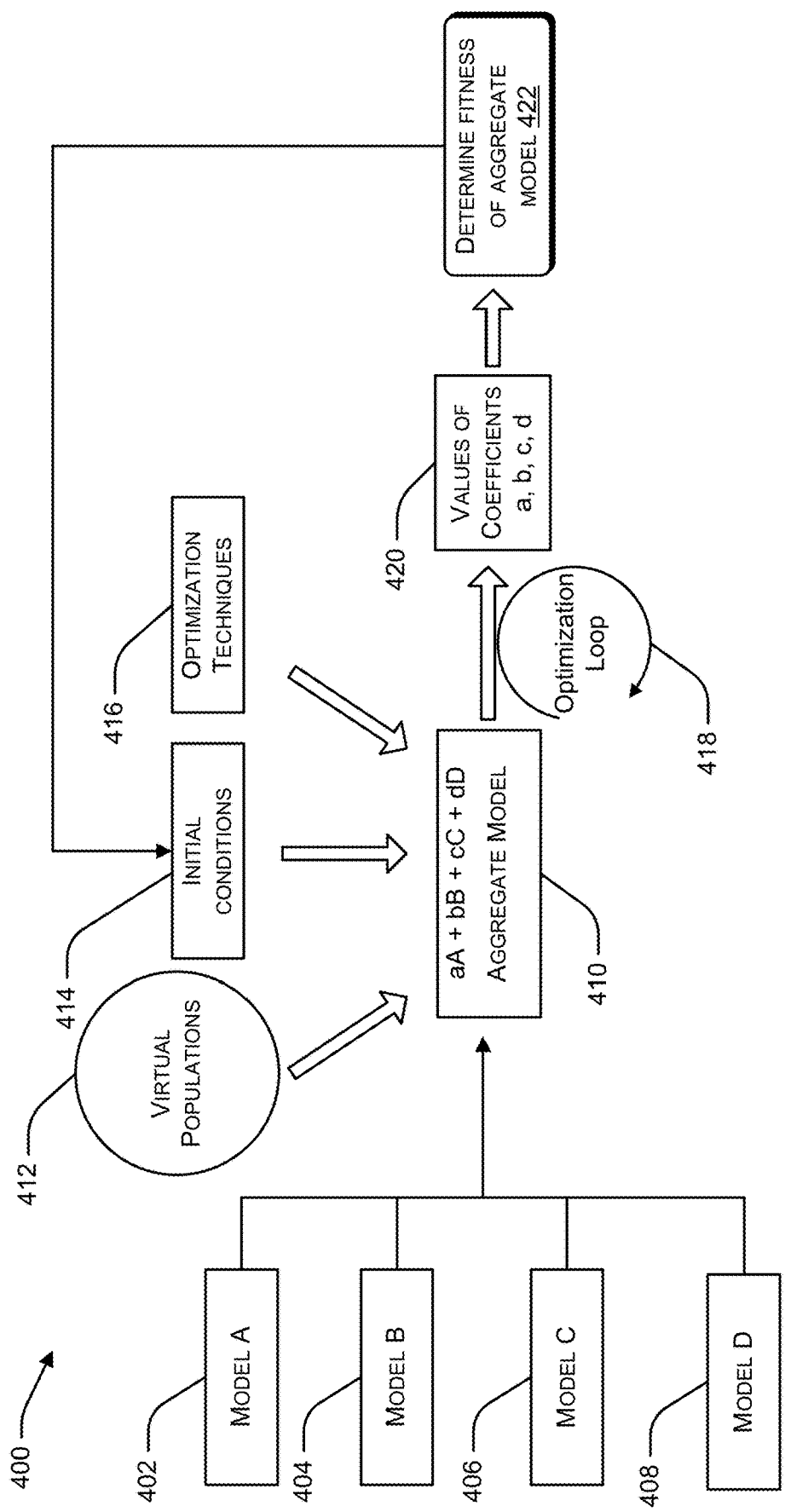
FIG. 4 shows a schematic diagram of a framework to determine a combination of models that predicts progression of a biological condition.

FIG. 4 shows a schematic diagram of a framework 400 to determine a combination of models that predicts progression of a biological condition. The framework 400 includes a first model 402, a second model 404, a third model 406, and a fourth model 408. The models 402, 404, 406, 408 can be derived from clinical data. In particular implementations, the models 402, 404, 406, 408 can be derived from clinical data corresponding to a particular biological condition such that the models 402, 404, 406, 408 can predict the progression of the biological condition. The framework 400 can determine the fitness of the combination of individual models 402, 404, 406, 408 in predicting the progression of the biological condition by evaluating an aggregate model 410. The aggregate model 410 can be a linear equation that includes variables corresponding to each model 402, 404, 406, 408 and coefficients a, b, c, and d, related to each model.

The aggregate model 410 can be evaluated using one or more virtual populations 412. The virtual populations 412 can be generated using information from populations that participated in the clinical trials used to produce the models 402, 404, 406, 408. In some cases, the virtual populations 412 can also be generated using information from populations other than those used to produce the models 402, 404, 406, 408, but corresponding to other clinical trials studying the progression of the same biological condition(s) as the clinical trials used to produce the models 402, 404, 406, 408.

In some implementations, the aggregate model 410 can be represented by the equation:

$$s(t_j, f_j, r_i, p_i) = \Sigma_j g((t_j \odot \{f_j(p_i) + e_{ij}\}) - g(\{r(p_i)\}))^2.$$

In this equation, s represents the fitness function that needs to be minimized, g represents the aggregate function and t is a term representing the model transformation. The models are represented by the term f and the virtual individuals that are being used to conduct the simulations are represented by p. A noise term is introduced with the variable e, while r represents the observed phenomenon from the clinical studies. The index i enumerates populations while the index j enumerates different models.

The aggregate model 410 can also be evaluated based on initial conditions 414. The initial conditions 414 can represent initial guesses regarding the coefficients for the different models included in the aggregate model 410. The initial conditions 414 regarding the coefficients can correspond to initial guesses of the starting points for contributions of the individual models in the evaluation of the aggregate model 410. The initial conditions 414 can also relate to the virtual populations 412. In these situations, the initial conditions 414 can indicate correlations between characteristics of individuals included in the virtual populations 412, such as increasing age corresponds to increasing blood pressure. When the initial conditions 414 relate to characteristics of the virtual populations 412, the initial conditions 414 can also indicate that values for a characteristic are static or not.

Further, the initial conditions 414 can include inclusion/exclusion criteria for the virtual populations 412, a hamming distance, or both.

In addition, the aggregate model 410 can be evaluated using optimization techniques 416. The optimization techniques 416 can correspond to one or more algorithms that can be used to solve the linear equation associated with the aggregate model 410 to determine the fitness of the models 402, 404, 406, 408 in predicting the progression of the biological condition. In some cases, the optimization techniques can include gradient descent techniques. In other instances, the optimization techniques can include evolutionary computation techniques. In particular implementations, the optimization techniques 416 can be directed to finding a local minimum that solves the linear equation of the aggregate model 410. In some cases, the local minimum can be determined after performing multiple iterations using the optimization techniques 416 in an optimization loop 418. The number of iterations included in the optimization loop 418 can correspond to a stopping criteria. In particular implementations, the stopping criteria can be a specified number of iterations, while in other situations, the stopping criteria can correspond to a value of a coefficient or other specified criteria.

At the local minimum, the values of the coefficients 420 can be determined. The values of the coefficients 420 can indicate a contribution of the respective models 402, 404, 406, 408 to predicting the progression of the biological condition. For example, the aggregate model 410 can be solved and the values of the coefficients 420 can be a=0.32, b=0.39, c=0.20, and d=0.09. The values for the coefficients can indicate the models that are the most dominant or most influential in determining outcomes for a given combination of model. In the illustrative example, model B can be identified as the model that is the most influential in determining outcomes for the aggregate model 410.

The process of evaluating the aggregate model 410 can continue at 422 by determining the fitness of the aggregate model 410 with the values of the coefficients 420. The fitness of the aggregate model 410 can be determined by comparing the results of the simulations with observed outcomes for a similar population. In some implementations, at least a portion of the simulations can be performed concurrently. The differences between the results of the simulations for each equation and the observed outcomes can be used to determine a fitness score for the initial iteration. Simulations for aggregate model 410 can then be performed for the subsequent guess combinations for the transformation parameters and the corresponding fitness scores can be determined based on the differences between the simulation results and the observed outcomes. If the fitness scores improve, that is if the difference between the simulations and the observed outcomes decreases, then the iterative process can continue with guesses in a similar direction until one or more criteria are satisfied.

In particular implementations, the transformation parameters/coefficients can be static, variable, scaled, and/or normalized. In some cases, groups of transformation parameters can be of the same type. For example, a first group of transformation parameters can be static, while another group of transformation parameters can be variable. The transformation parameter groups can be formed, in some situations, based on a condition associated with a state of a biological condition. For example, a first group of transformation parameters/coefficients can be associated with disease states related to coronary heart disease for individuals with diabetes, while a second group of transformation parameters/coefficients can be associated with disease states related to stroke for individuals with diabetes. In various implementations, the transformation parameter groups can be associated with various inclusion criteria, exclusion criteria, and Hamming distance criteria. That is, a first group of transformation parameters can be defined by a first set of criteria, while a second group of transformation parameters can be defined by a second set of criteria. In some situations, the transformation parameters included in each group can change as the iterative process to solve the transformation proceeds. During the iterative process to optimize the aggregate model 410, the values of the static type transformation parameters will remain constant. Additionally, if a transformation parameter falls outside of one or more of the criteria during one or more iterations of the optimization process, the value of the transformation parameter can be truncated to stay within each of the optimization criteria. In situations where a transformation parameter is a scaled transformation parameter, during the individual optimization steps, the scaled transformation parameters can be divided by the sum of the parameters and multiplied by a scaling factor. The scaling factor can be associated with the particular parameter group of the scaled transformation parameter. In other implementations, during the individual optimization steps, the scaled transformation parameters can be divided by the norm of the sum of the parameters and multiplied by a normalizing value. The normalizing value can be associated with the particular parameter group of the scaled transformation parameter.

Figures 5A, 5B:
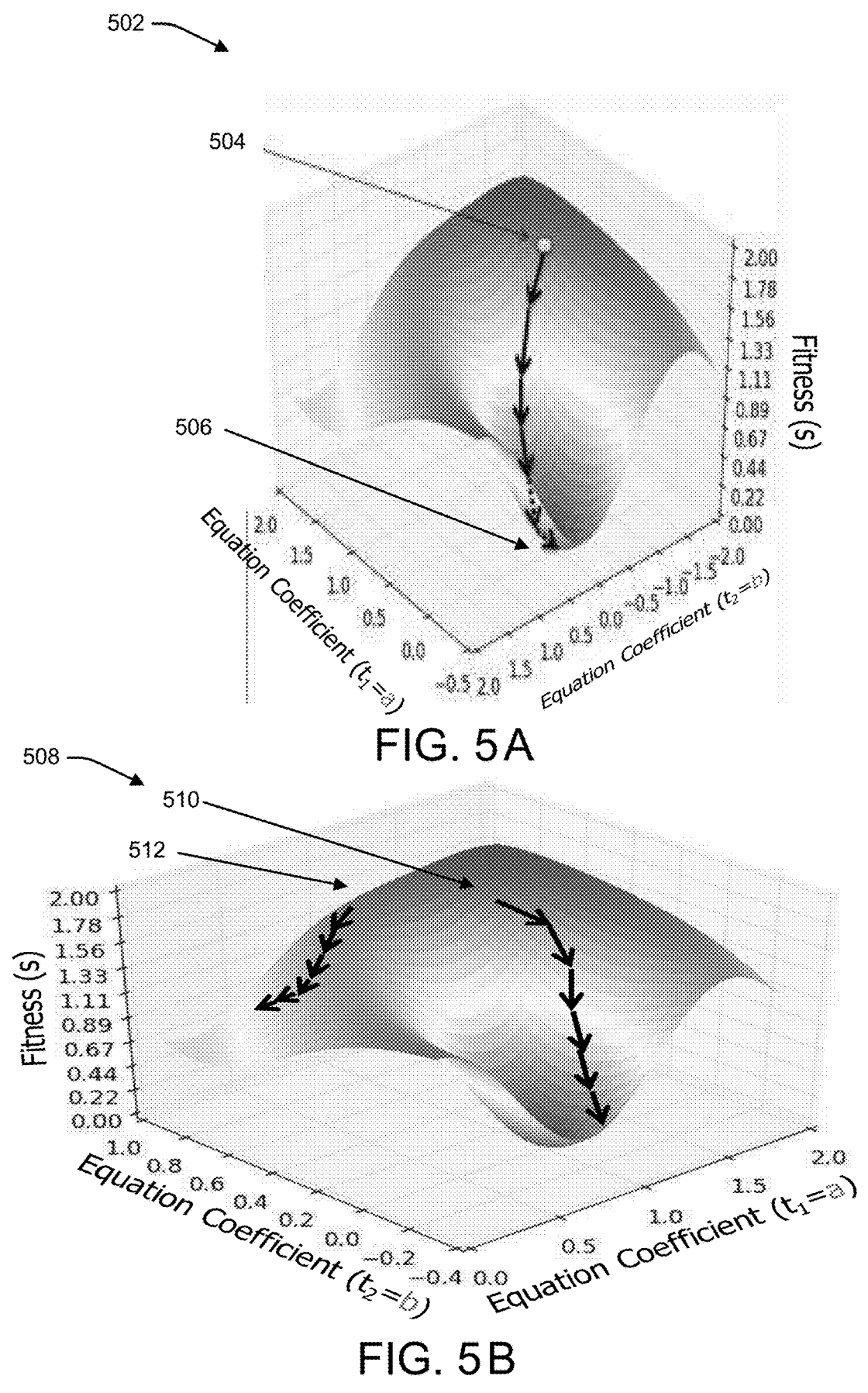

FIG. 5A shows an example implementation 502 of using gradient descent techniques to determine a local minimum for an aggregate fitness function that identifies the optimal contributions of each individual model to the aggregate fitness function, while FIG. 5B shows an example of using multiple initial guesses for the optimization process. The gradient descent technique provides cooperative features to determine an amount of contribution of each model included in an aggregate model. With each iteration of the gradient descent algorithm, the solution moves closer to a local minimum. The gradient descent algorithm can start at 504 and work towards 506. The use of gradient descent optimization techniques allows the optimal combination of multiple models to be determined in continuous parameter space rather than computing all model combinations in discrete parameter space, which reduces the processing resources and memory resources utilized to determine the aggregate model because the resources simply increase linearly per parameter for each gradient descent iteration as more equations are added rather than close to exponentially.

Figure 6:
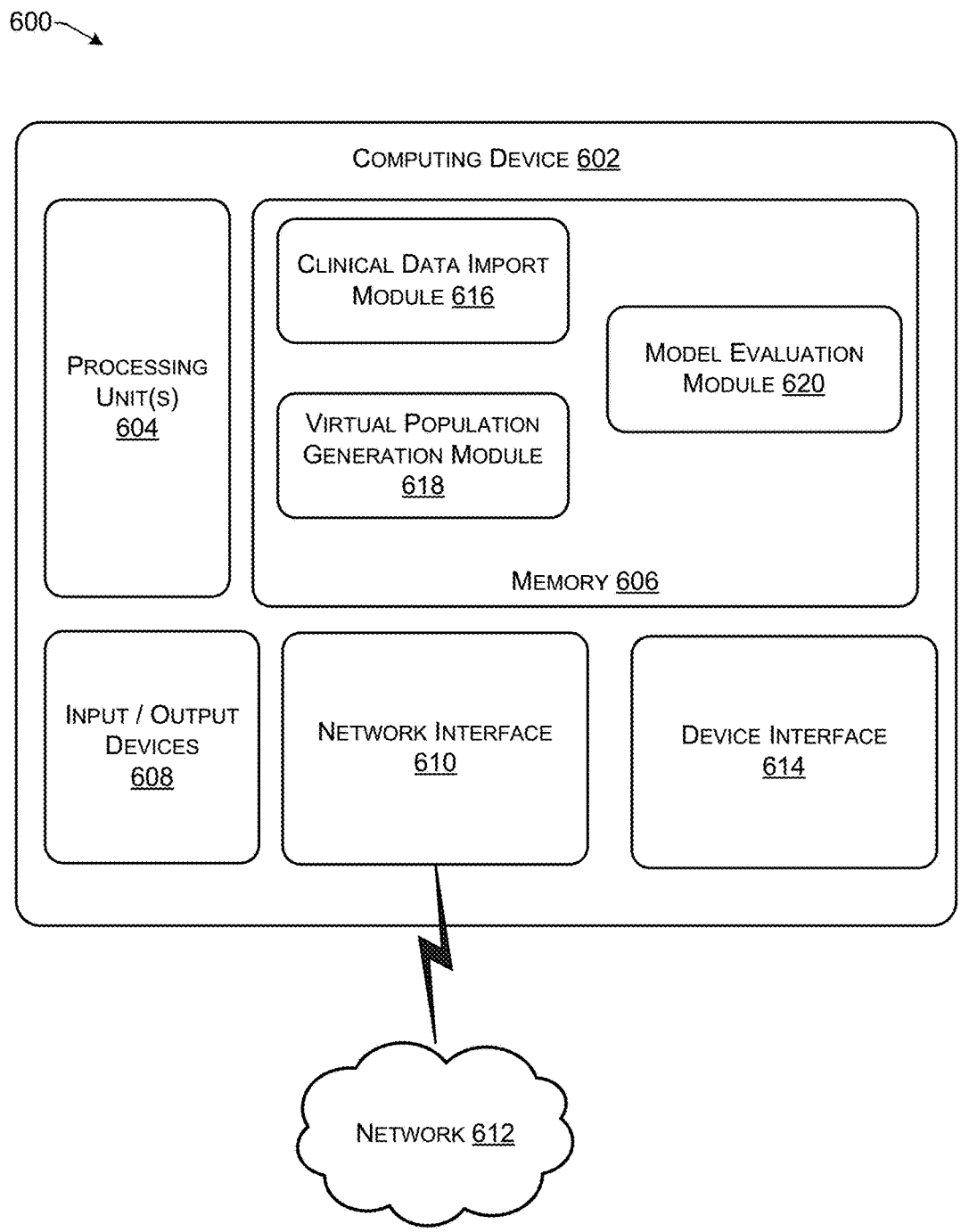
FIG. 6 shows a block diagram of an example computing device to evaluate models derived from clinical data using a cooperative framework with some competitive elements.

The second example 508 included in FIG. 5B shows a number of initial guesses 510, 512 that can be evaluated. For each initial guess 510, 512, a gradient descent algorithm can be used to determine a local minimum. The use of the gradient descent algorithm to identify the local minimum can correspond to cooperative elements of the implementations described herein. The fitness of the end result of the coefficients determined for the local minima for each initial guess 510, 512 can be evaluated with respect to each other. The evaluation of the differing coefficients with respect to observed outcomes for each initial guess 510, 512 can represent certain competitive aspects of the implementations described herein FIG. 6 shows a block diagram of an example computing device 600 to evaluate models derived from clinical data using a cooperative framework with some competitive elements. The computing device 602 can be implemented with one or more processing unit(s) 604 and memory 606, both of which can be distributed across one or more physical or logical locations. For example, in some implementations, the operations described as being performed by the computing device 602 can be performed by multiple computing devices. In some cases, the operations described as being performed by the computing device 602 can be performed in a cloud computing architecture.

The processing unit(s) 604 can include any combination of central processing units (CPUs), graphical processing units (GPUs), single core processors, multi-core processors, application-specific integrated circuits (ASICs), programmable circuits such as Field Programmable Gate Arrays (FPGA), and the like. In one implementation, one or more of the processing units(s) 604 can use Single Instruction Multiple Data (SIMD) parallel architecture. For example, the processing unit(s) 604 can include one or more GPUs that implement SIMD. One or more of the processing unit(s) 604 can be implemented as hardware devices. In some implementations, one or more of the processing unit(s) 604 can be implemented in software and/or firmware in addition to hardware implementations. Software or firmware implementations of the processing unit(s) 604 can include computer- or machine-executable instructions written in any suitable programming language to perform the various functions described. Software implementations of the processing unit(s) 604 may be stored in whole or part in the memory 606.

Alternatively, or additionally, the functionality of computing device 602 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Memory 606 of the computing device 602 can include removable storage, non-removable storage, local storage, and/or remote storage to provide storage of computer-readable instructions, data structures, program modules, and other data. The memory 606 can be implemented as computer-readable media. Computer-readable media includes at least two types of media: computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media can embody computer-readable instructions, data structures, program modules, or other data in a modulated data signal, such as a carrier wave, or other transmission mechanism. As defined herein, computer-readable storage media and communications media are mutually exclusive.

The computing device 602 can include and/or be coupled with one or more input/output devices 608 such as a keyboard, a pointing device, a touchscreen, a microphone, a camera, a display, a speaker, a printer, and the like. Input/output devices 608 that are physically remote from the processing unit(s) 604 and the memory 606 can also be included within the scope of the input/output devices 608.

Also, the computing device 602 can include a network interface 610. The network interface 610 can be a point of interconnection between the computing device 602 and one or more networks 612. The network interface 610 can be implemented in hardware, for example, as a network interface card (NIC), a network adapter, a LAN adapter or physical network interface. The network interface 610 can be implemented in software. The network interface 610 can be implemented as an expansion card or as part of a motherboard. The network interface 610 can implement electronic circuitry to communicate using a specific physical layer and data link layer standard, such as Ethernet or Wi-Fi. The network interface 610 can support wired and/or wireless communication. The network interface 610 can provide a base for a full network protocol stack, allowing communication among groups of computers on the same local area network (LAN) and large-scale network communications through routable protocols, such as Internet Protocol (IP).

The one or more networks 612 can include any type of communications network, such as a local area network, a wide area network, a mesh network, an ad hoc network, a peer-to-peer network, the Internet, a cable network, a telephone network, a wired network, a wireless network, combinations thereof, and the like.

A device interface 614 can be part of the computing device 602 that provides hardware to establish communicative connections to other devices. The device interface 614 can also include software that supports the hardware. The device interface 614 can be implemented as a wired or wireless connection that does not cross a network. A wired connection may include one or more wires or cables physically connecting the computing device 602 to another device. The wired connection can be created by a headphone cable, a telephone cable, a SCSI cable, a USB cable, an Ethernet cable, FireWire, or the like. The wireless connection may be created by radio waves (e.g., any version of Bluetooth, ANT, Wi-Fi IEEE 802.11, etc.), infrared light, or the like.

The computing device 602 can include multiple modules that may be implemented as instructions stored in the memory 606 for execution by processing unit(s) 604 and/or implemented, in whole or in part, by one or more hardware logic components or firmware. The memory 606 can be used to store any number of functional components that are executable by the one or more processors processing units 604. In many implementations, these functional components can comprise instructions or programs that are executable by the one or more processing units 604 and that, when executed, implement operational logic for performing the operations attributed to the computing device 602. Functional components of the computing device 602 that can be executed on the one or more processing units 604 for evaluating models that predict the progression of a biological condition, as described herein, include a clinical data import module 616, a virtual population generation module 618, and a model evaluation module 620. One or more of the modules, 616, 618, 620 can be used to implement frameworks 100, 200, 300, 400, of FIG. 1, FIG. 2, FIG. 3, FIG. 4, and produce the examples of FIG. 5A and FIG. 5B.

The clinical data import module 616 can include computer-readable instructions that when executed by the one or more processing units 604 cause the computing device to extract data about one or more clinical trials from at least one database. In some cases, the database can be a private database maintained by one or more entities, such as an insurance company, a university, a health provider, combinations thereof, and so forth. In other situations, the database can be a public database maintained by one or more entities, such as a governmental entity. In an illustrative example, the database can include the website clinicaltrials.gov. The information stored in the one or more databases can include summary information for populations that have participated in clinical studies. The summary information can include values, such as mean, median, average, and the like, for different characteristics of a population (e.g., age, weight, cholesterol level, etc.). In particular implementations, the one or more databases may include more individualized information about the population, while still protecting the privacy of the individuals. For example, the databases can include information indicating a number of individuals of a particular age or a number of individuals of a particular weight.

The data obtained from the one or more databases can also include outcomes data that indicates the results of the clinical studies. The results of the clinical studies can indicate summary data and/or individualized data regarding the progression of biological conditions of individuals that participated in the clinical studies. The outcomes data can, in some cases, indicate a number of individuals that meet criteria for one or more biological conditions and/or that meet criteria for a state of a biological condition. For example, the outcomes data can indicate a number of individuals that suffered a stroke, a number of individuals that died during the clinical study, a number of individuals that have blood pressure within a specified range, and the like.

After obtaining information from the one or more databases, the clinical data import module 616 can filter the information according to one or more criteria. The one or more criteria can be included in a query of the extracted data. In particular implementations, the data can be filtered according to import instructions that modify the data extracted from the clinical studies database(s). In some situations, the data extracted from the database can be filtered and the data can be formatted according to particular templates. In additional implementations, conversion factors can be utilized that convert data from one set of units to another set of units. In various implementations, the instructions utilized to filter data extracted from a clinical studies database can be modified for filtering information from clinical studies that correspond to different biological conditions. Also, some features of previously utilized instructions can be re-used to optimize the resources utilized to filter the clinical studies information. In illustrative implementations, the instructions utilized to filter data obtained from a clinical studies database can modify the data such that the data can be utilized by algorithms, techniques, and engines that evaluate models that predict the progression of biological conditions.

The virtual population generation module 618 can include computer-readable instructions that when executed by the one or more processing units 604 cause the computing device 602 to generate one or more virtual populations. A virtual population can include characteristics of each individual included in the virtual population. For example, each individual of a virtual population can have a height, a weight, an age, a gender, a blood pressure, a cholesterol level, and so forth. The virtual population generation module 618 can utilize population summary data obtained from the clinical study data to generate specific information for each individual included in the virtual population.

In some cases, the virtual population generation module 618 can implement object oriented techniques in regard to the generation of a virtual population. For example, the virtual population generation module 618 can obtain instructions indicating that a virtual population is to be generated that derives characteristics from additional populations. To illustrate, a virtual population can be generated that derives a first set of characteristics from a first population and a second set of characteristics from a second population. In particular implementations, the first population and the second population can be other virtual populations, actual populations, or a combination thereof. In illustrative implementations, objectives, such as average blood pressure and a corresponding standard deviation or upper and lower blood pressure limits, can be provided by a population. To meet objectives provided by one or more populations, the virtual population generation module 618 can produce a number of virtual individuals that have certain characteristics and then filter the number of virtual individuals to produce a smaller population that meets the objectives as close as possible within computing constraints. Thus, if a rule or an objective indicates that the age range for the virtual population is to be from 45 to 79, the virtual population generation module 618 can remove any virtual individuals that have ages outside of the specified age range. In a particular illustrative implementation, the virtual population generation module 618 can choose a set of virtual individuals that best meet the objectives provided, such as the best 1000 virtual individuals out of 10,000 virtual individuals generated by the virtual population generation module 618.

The model evaluation module 620 can include computer-readable instructions that when executed by the one or more processing units 604 cause the computing device 602 to evaluate models that predict the progression of one or more biological conditions. The model evaluation module 620 can obtain one or more models that predict the progression of a biological condition. The one or more models can be produced from clinical study data. The model evaluation module 620 can utilize cooperative techniques to determine a fitness of a combination of the models. For example, an aggregate model predicting the progression of a biological condition can be produced from a plurality of models. In some cases, the aggregate model can be represented by an equation. In a particular illustrative example, the aggregate model can be represented by a linear equation having functions that correspond to each individual model of the aggregate model and a respective coefficient that corresponds to each function.

The model evaluation module 620 can evaluate the aggregate model with respect to at least one virtual population generated by the virtual population generation module 618. In various implementations, the model evaluation module 620 can utilize one or more algorithms to determine the values for the functions represented in the aggregate model. In a particular example, the model evaluation module 620 can utilize a gradient descent algorithm to identify a local minimum and identify the values of the functions for each model at the local minimum. The values of the functions can indicate a contribution or importance of each model of the aggregate equation. In some situations, a number of iterations of the gradient descent algorithm can be performed by the model evaluation module 620 to determine the local minimum for the aggregate model with each iteration getting closer to the local minimum.

The fitness of a particular combination of models included in the aggregate models and based on a set of coefficients can be used to determine outcomes for a virtual population.

In illustrative implementations, the outcomes for the virtual population can be determined by evaluating the individuals included in the virtual population on a yearly basis and tracking the progression of a biological condition until the death of the virtual individuals caused either by a particular biological condition being studied or mortality caused by another biological condition. In particular implementations, the virtual population can correspond to an actual population that was used to derive at least one of the models included in the aggregate model. In some cases, the virtual population can correspond to a combination of actual populations that were used to produce the models of the aggregate model. The model evaluation module 620 can evaluate the fitness of the particular combination of models by comparing the simulated outcomes from the aggregate model and the virtual population with actual outcomes from a clinical study. In some implementations, multiple runs can be performed for an aggregate model and a corresponding virtual population to determine consistency between the outcomes for the aggregate model.

In various implementations, the models of the aggregate model can be evaluated using a set of initial conditions. The set of initial conditions can include initial guesses for the coefficients of each model. The set of initial conditions can also indicate constraints for the virtual population being generated. The set of initial conditions can also indicate assumptions or hypotheses to be evaluated, such as the effects that one characteristic of an individual (e.g., age) can have on another characteristic (e.g., cholesterol). The model evaluation module 620 can evaluate an aggregate model under a number of sets of initial conditions to determine the viability of various assumptions or hypotheses being tested using the aggregate model. For example, the initial conditions can include a hypothesis that treatment options for a biological condition improve outcomes over time. Continuing with this example, the aggregate model can be evaluated when the hypothesis is true and when the hypothesis is false. The outcomes of the evaluation of the aggregate model can be compared to actual outcomes to determine the viability of the hypothesis. To illustrate, the hypothesis that outcomes are improved as time progresses due to improved treatments over time can be more likely when the simulated outcomes are closer to the actual outcomes than the simulated outcomes when the assumption is not factored into the results.

Figure 7:
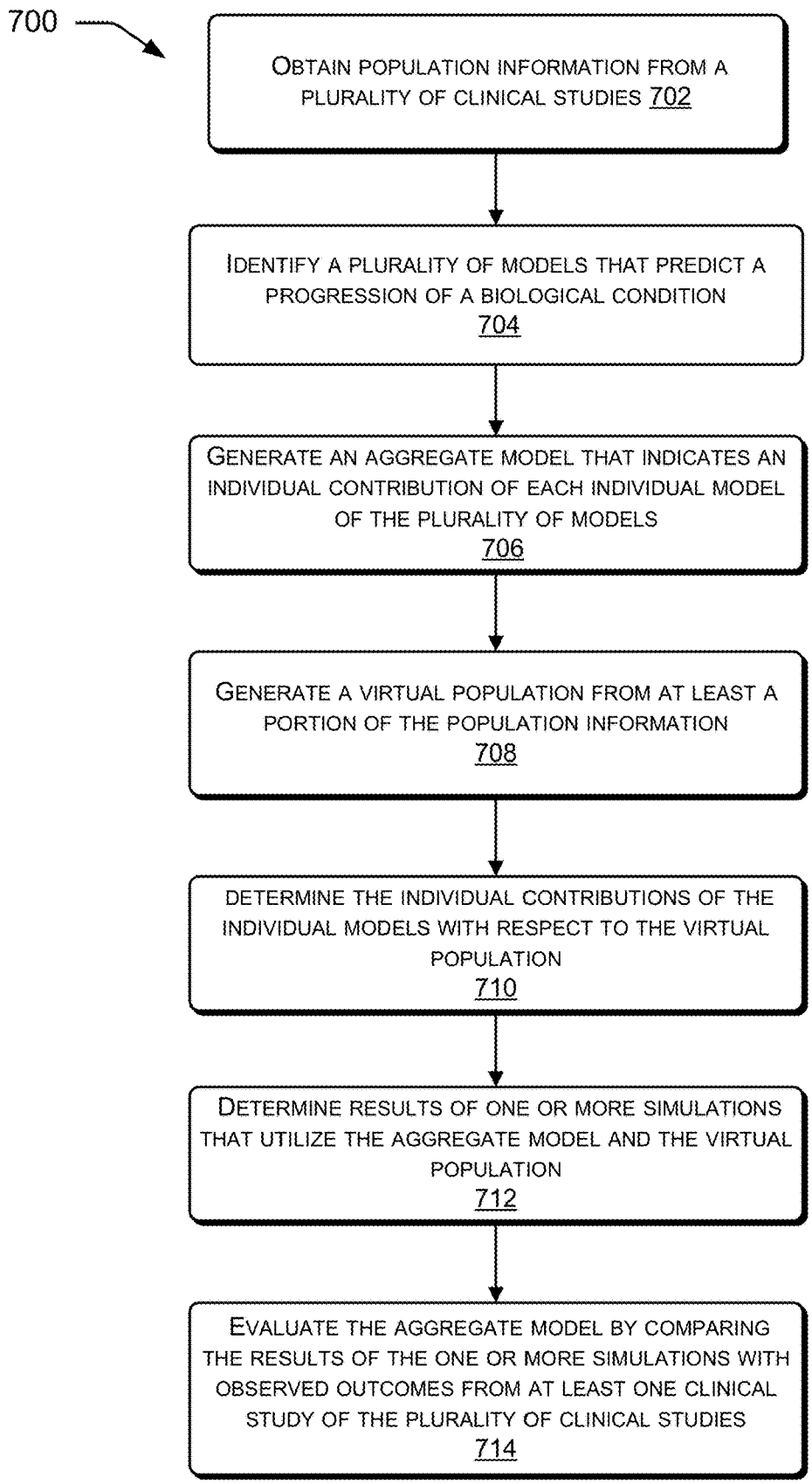
FIG. 7 is a flow diagram of an example process to evaluate models derived from clinical data using a cooperative framework with some competitive elements.

FIG. 7 is a flow diagram of an example process 700 to evaluate models derived from clinical data using a cooperative framework with some competitive elements. The operations illustrated in the example flow diagram of FIG. 7 can be implemented in hardware, software, or a combination thereof. In the context of software, the blocks can represent computer-executable instructions stored on one or more computer-readable media that, when executed by one or more processors, perform the operations recited in the blocks of the example flow diagram. The order in which the operations are described should not be construed as a limitation. Any number of the described blocks can be combined in any order and/or in parallel to implement the process 700, or alternative processes, and not all of the blocks need be executed.

At 702, the process 700 includes obtaining population information from a plurality of clinical studies. In some situations, the population information can be obtained from an online database. The population information can include summary information for one or more populations. The summary information can include at least one statistical measure for at least one characteristic of the one or more populations. For example, the summary information can include a mean, median, mode, average, a specific number, a proportion, a statistical distribution (e.g., $25^{th}$ percentile) of a characteristic of a population, such as blood pressure, cholesterol level, height, etc.

In particular implementations, after extracting the population information from the online database, the population information can be filtered. In various implementations, the population information can be filtered according to a query to produce filtered population information. In additional implementations, the query can be included in import instructions that are used to filter the population information. In certain implementations, the filtered population information can be formatted according to a predetermined template to produce formatted population information. The formatted population information can be merged with prior population information stored in a template file. For example, the template file can include information that had been previously extracted from the online database corresponding to a different population that participated in a different clinical study.

In particular implementations, the formatting of the population information can be related to units of measurement of characteristics of individuals included in populations that participated in the clinical studies. For example, the population information can include values of a first characteristic related to the biological condition where the values are associated with a first unit of measurement. The values of the first characteristic can be converted from the first unit of measurement to a second unit of measurement. In some cases, the conversion from the first unit to the second unit can be specified by instructions used to obtain the population data. Additionally, the population information can include additional values of a second characteristic related to the disease where the additional values are associated with a third unit of measurement. The additional values of the second characteristic can be converted from the third unit of measurement to the second unit of measurement. In particular implementations, the first characteristic can have a first rate of conversion from the first unit of measurement to the second unit of measurement and the second characteristic can have a second rate of conversion from the third unit of measurement to the second unit of measurement. In an illustrative example, HDL levels can be converted from mg/dL to mmol/L using a first rate of conversion and triglycerides can be converted from mg/dL to mmol/L using a second rate of conversion.

At 704, the process 700 includes identifying a plurality of models that predict a progression of a biological condition. For example, the plurality of models can include a first model that is derived from at least one first clinical study and a second model that is derived from at least one second clinical study. The progression of the disease can include a plurality of states. In some cases, the progression of the disease can end in death.

At 706, the process 700 includes generating an aggregate model that indicates an individual contribution of each individual model of the plurality of models. The aggregate model can include an equation that corresponds to the individual models of the plurality of models and each model is associated with a value that indicates the contribution of the individual model.

At 708, the process 700 includes generating a virtual population from at least a portion of the population information. In some implementations, generating the virtual population can implement object-oriented techniques. For example, generating the virtual population can include generating a first object that includes first one or more rules related to determining values of characteristics of and includes first one or more objectives defining statistics for a first population of the plurality of populations. Additionally, generating the virtual population can also include generating a second object that includes one or more second rules related to determining values of characteristics and includes one or more second objectives defining statistics related to a second population of the plurality of populations. In these situations, the virtual population can include an object that inherits from the first object and the second object.

In various implementations, the object-oriented techniques can be utilized when conflicts arise between rules and/or objectives included in the particular objects utilized to generate the virtual population. The objectives can specify values for statistics of individuals included in the virtual population. To illustrate, a conflict can be determined between at least one first rule of the first object and at least one second rule of the second object. In other scenarios, a conflict can be determined between at least one first objective of the first object and at least one second objective of the second object. In a particular illustrative example, generating the virtual population can include generating a plurality of virtual individuals that satisfy one or more of: a particular first rule that does not conflict with at least one of the one or more second rules; a particular first objective that does not conflict with at least one of the one or more second objectives; at least one second rule that conflicts with at least one first rule; or at least one second objective that conflicts with at least one first objective. objectives that specify values for statistics of individuals included in the virtual population.

In an illustrative example, a virtual population object can be comprised of a first object that includes a first rule indicating that the age of virtual individuals is to be from 20 to 30 and a second object that includes a second rule indicating that the age of virtual individuals is to be from 25 to 35. The virtual population object can indicate that the second object supersedes the first object. In the case of this conflict, a virtual population is generated with virtual individuals having ages from 25 to 35.

Additionally, a virtual population object can be comprised of a first object that includes a first objective indicating that virtual population is to have a mean age of 25 and a second object that includes a second objective indicating that the virtual population is to have an average age of 32. The virtual population object can also indicate that the second object supersedes the first object. In the case of this conflict, a virtual population is generated with virtual individuals having an average age of 32.

A virtual population object can also inherit specific data for virtual individuals. For example, a virtual population object can be comprised of an object that includes particular ages of individuals, such as 22, 22, 23, 24, 24, 24, 25, 25, 26, 28, etc. In these situations, the virtual individuals of the virtual population have the same ages as the individuals included in the object from which the virtual population object inherits age data.

Object oriented techniques can also be used when virtual individuals of the virtual population are missing values for a characteristic. For example, an object can be identified that includes individuals having particular values of the characteristic. The virtual individuals of the virtual population can then be modified to have at least a portion of the particular values of the characteristic included in the object.

At 710, the process 700 includes determining the individual contributions of the individual models with respect to the virtual population. In some cases, the individual contributions of the individual models can be determined by optimizing the aggregate model using cooperative techniques. In certain implementations, determining the individual contributions of the individual models with respect to a plurality of virtual populations can include determining a local minimum of the aggregate model for the plurality of virtual populations. The local minimum, in various implementations, can be determined using a gradient descent algorithm such that the individual models cooperate during optimization and that is implemented over a number of iterations.

At 712, the process 700 includes determining results of one or more simulations that utilize the aggregate model and the virtual population. In some cases, the results of the one or more simulations are determined using a first set of initial conditions and additional results of one or more additional simulations can be determined that utilize the aggregate model, the virtual population, and that use a second set of initial conditions. The first set of initial conditions can include first estimates of the individual contributions of the individual models of the plurality of models, a first hypothesis, a first relationship between characteristics related to the biological condition, or a combination thereof. Additionally, the second set of initial conditions can include second estimates of the individual contributions of the individual models of the plurality of models, a second hypothesis that is a complement of the first hypothesis, a second relationship between characteristics related to the biological condition, or a combination thereof. In an illustrative implementation, the first hypothesis can be directed to an assumption that treatment for the biological condition improves over time, while the complement to the first hypothesis is directed to an assumption that treatment for the biological condition does not improve over time.

In some implementations, a first fitness of the first set of initial conditions can be determined based at least partly on first results of a first number of simulations for a plurality of virtual populations with regard to the observed outcomes. Also, a second fitness of the second set of initial conditions based at least partly on second results of a second number of simulations for the plurality of virtual populations with regard to the observed outcomes. The first fitness and the second fitness can be compared to evaluate the first set of initial conditions with respect to the second set of initial conditions.

At 714, the process 700 includes evaluating the aggregate model by comparing the results of the one or more simulations with observed outcomes from at least one clinical study of the plurality of clinical studies. The difference between the simulated outcomes and the observed outcomes can indicate the fitness of the aggregate model. In particular implementations, the greater the difference between the simulated outcomes and the observed outcomes, the less fit the aggregate model and the smaller the difference between the simulated outcomes and the observed outcomes, the more fit the aggregate model.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for their particular cited teachings as well as for all that they disclose.

The invention claimed is:

1. A method comprising:
   obtaining, from at least one online database, clinical study information, the clinical study information including information corresponding to a number of models that predict a progression of one or more diseases and population summary data that indicates characteristics of groups of individuals involved in a plurality of clinical studies with respect to the one or more diseases;
   identifying a first model from among the number of models that predicts the progression of a disease of the one or more diseases, wherein the first model is derived from a first portion of the clinical study information and the progression of the disease includes a plurality of states;
   identifying a second model from among the number of models that predicts the progression of the disease, wherein the second model is derived from a second portion of the clinical study information;
   generating an aggregate model that includes a first coefficient corresponding to the first model and a second coefficient corresponding to the second model,
   generating, based on the population summary data, a virtual population including a number of virtual individuals;
   determining, based on data related to virtual individuals included in the virtual population, first simulated outcomes of the aggregate model using a first value of the first coefficient and a second value of the second coefficient, wherein:
      individual first simulated outcomes of the first simulated outcomes indicate a first probability of a virtual individual of the virtual population progressing from one state of the disease to another state of the disease over a period of time;
      the first value of the first coefficient corresponds to a first amount of contribution of the first model in determining the first simulated outcomes; and
      the second value of the second coefficient corresponds to a second amount of contribution of the second model in determining the first simulated outcomes;
   analyzing the first simulated outcomes with respect to first observed outcomes obtained from the clinical study information to determine first differences between the first simulated outcomes and the first observed outcomes;
   modifying, based on the first differences, at least one of the first coefficient or the second coefficient to determine second simulated outcomes of the aggregate model based on the data related to the virtual individuals included in the virtual population; and
   determining a measure of fitness of the aggregate model based on differences between the second simulated outcomes and second observed outcomes obtained from the clinical study information and based on a fitness function corresponding to the aggregate model moving toward a local minimum.

2. The method of claim 1, further comprising:
   obtaining the population summary data from at least one online database using a query; and
   filtering the population information according to import instructions to produce filtered population summary data, wherein the query is included in the import instructions used to filter the population summary data.

3. The method of claim 2, further comprising:
   formatting the filtered population summary data according to a predetermined template to produce formatted population summary data; and
   merging the formatted population summary data with prior population summary data stored in a template file.

4. The method of claim 1, wherein:
   the clinical study information includes at least one first clinical study that includes the first model and at least one second clinical study that includes the second model; and
   the population summary data includes summary information including at least one statistical measure for at least one characteristic of one or more groups of individuals included in at least one of the at least one first clinical study or the at least one second clinical study.

5. The method of claim 1, further comprising:
   determining that the population summary data includes values of a first characteristic related to the disease, the values being associated with a first unit of measurement; and
   converting the values of the first characteristic from the first unit of measurement to a second unit of measurement specified by instructions used to obtain the population summary data.

6. The method of claim 5, further comprising:
   determining that the population summary data includes additional values of a second characteristic related to the disease, the additional values being associated with a third unit of measurement; and
   converting the additional values of the second characteristic from the third unit of measurement to the second unit of measurement.

7. The method of claim 6, wherein the first characteristic has a first rate of conversion from the first unit of measurement to the second unit of measurement and the second characteristic has a second rate of conversion from the third unit of measurement to the second unit of measurement.

8. The method of claim 1, wherein the virtual population is generated according to objectives that specify values for statistics of virtual individuals included in the virtual population.

9. A method comprising:
   obtaining, from at least one online database, clinical study information, the clinical study information including information corresponding to a number of models that predict a progression of one or more biological conditions and population summary data that indicates characteristics of groups of individuals involved in a plurality of clinical studies with respect to the one or more biological conditions;

identifying, from among the number of models, a plurality of models that predict a progression of a biological condition of the one or more biological conditions;

generating an aggregate model that includes a plurality of coefficients, individual coefficients of the plurality of coefficients indicating an individual contribution of an individual model of the plurality of models to a fitness function of the aggregate model;

generating one or more virtual populations based on the population summary data;

performing a plurality of iterations of an optimization process for the fitness function, individual iterations of the plurality of iterations including:
  determining a respective value of one or more coefficients of the plurality of coefficients,
  determining simulated outcomes for the aggregate model for virtual individuals included in a virtual population of the one or more virtual populations, individual simulated outcomes being influenced by a probability of a virtual individual included in the virtual population progressing from at least one state of the biological condition to at least one additional state of the biological condition over a period of time; and
  determining a measure of fitness of the aggregate model for the individual iteration based on differences between observed outcomes of individuals included in the clinical study information and the simulated outcomes for the individual iteration of the optimization process, the measure of fitness to move the fitness function toward a local minimum; and determining, after completion of the optimization process, values of respective coefficients of the plurality of coefficients at the local minimum of the fitness function.

10. The method of claim 9, wherein first simulated outcomes of a first iteration of the plurality of iterations of the optimization process are determined using a first set of initial conditions that include a first value of a first coefficient of a first model included in the aggregate model and a second value of a second coefficient of a second model included in the aggregate model, and the operations further comprise:
  determining second simulated outcomes of a second iteration of the plurality of iterations of the optimization process utilizing the aggregate model and the virtual population and that utilize a second set of initial conditions that include a first additional value of the first coefficient of the first model and a second additional value of the second coefficient of the second model.

11. The method of claim 10, wherein:
the first set of initial conditions include first estimates of the individual contributions of the individual models of the plurality of models, a first hypothesis, a first relationship between characteristics related to the biological condition, or a combination thereof; and
the second set of initial conditions include second estimates of the individual contributions of the individual models of the plurality of models, a second hypothesis that is a complement of the first hypothesis, a second relationship between characteristics related to the biological condition, or a combination thereof.

12. The method of claim 10, further comprising:
determining a first measure of fitness for the aggregate model with respect to the first set of initial conditions based at least partly on the first simulated outcomes with regard to the observed outcomes;
determining a second measure of fitness for the aggregate model with respect to the second set of initial conditions based at least partly on the second simulated outcomes with regard to the observed outcomes; and
comparing the first measure of fitness with the second measure of fitness.

13. The method of claim 9, wherein:
a first coefficient of the plurality of coefficients is static and has a first value that does not change during the optimization process; and
a second coefficient of the plurality of coefficient is variable and has a second value that does change during the optimization process.

14. The method of claim 9, wherein the local minimum is determined using a gradient descent algorithm such that the individual models of the plurality of models cooperate during the optimization process.

15. A system comprising:
one or more processing units;
memory including computer-readable instructions that when executed by the one or more processing units perform operations comprising;
obtaining, from at least one online database, clinical study information, the clinical study information including information corresponding to a number of models that predict a progression of one or more one or more biological conditions and population summary data that indicates characteristics of groups of individuals involved in a plurality of clinical studies with respect to the one or more biological conditions;
identifying, from among the number of models, a plurality of models that predict a progression of a biological condition of the one or more biological conditions;
generating an aggregate model that includes a plurality of coefficients, individual coefficients of the plurality of coefficients indicating an individual contribution of an individual model of the plurality of models to a fitness function of the aggregate model;
generating one or more virtual populations based on the population summary data;
performing a plurality of iterations of an optimization process for the fitness function, individual iterations of the plurality of iterations including:
  determining a respective value of one or more coefficients of the plurality of coefficients,
  determining simulated outcomes for the aggregate model for virtual individuals included in a virtual population of the one or more virtual populations, individual simulated outcomes influenced by a probability of a virtual individual included in the virtual population progressing from at least one state of the biological condition to at least one additional state of the biological condition over a period of time; and
  determining a measure of fitness of the aggregate model for the individual iteration based on differences between observed outcomes of individuals included in the clinical study information and the simulated outcomes for the individual iteration of the optimization process, the measure of fitness to move the fitness function toward a local minimum; and determining, after completion of the optimization process, values of respective coefficients of the plurality of coefficients at the local minimum of the fitness function.

16. The system of claim 15, wherein the operations further comprise:

generating a first object that includes one or more first rules related to determining values of characteristics of first virtual individuals and includes one or more first objectives defining statistics for a first group of individuals included in the clinical study information; and generating a second object that includes one or more second rules related to determining values of characteristics second virtual individuals and includes one or more second objectives defining statistics related to a second group of individuals included in the clinical study information.

17. The system of claim 16, wherein the virtual population is an object that inherits from the first object and the second object.

18. The system of claim 17, wherein the operations further comprise at least one of:

determining a conflict between at least one first rule of the first object and at least one second rule of the second object; or determining a conflict between at least one first objective of the first object and at least one second objective of the second object.

19. The system of claim 17, wherein generating the virtual population includes generating a plurality of virtual individuals that satisfy one or more of:

a first rule that does not conflict with at least one of the one or more second rules;

a first objective that does not conflict with at least one of the one or more second objectives;

at least one second rule that conflicts with at least one first rule; or at least one second objective that conflicts with at least one first objective.

20. The system of claim 15, wherein the operations further comprise:

determining that virtual individuals of the virtual population are missing values for a characteristic;

identifying an object that includes a group of individuals included in the clinical study information having values of the characteristic; and modifying the virtual individuals of the virtual population to have at least a portion of the values of the characteristic included in the object.

* * * * *